(12) United States Patent
Seeber

(10) Patent No.: US 10,881,268 B2
(45) Date of Patent: Jan. 5, 2021

(54) DEVICE TO SET AND RETRIEVE A REFERENCE POINT DURING A SURGICAL PROCEDURE

(71) Applicant: avateramedical GmbH, Jena (DE)

(72) Inventor: Marcel Seeber, Jena (DE)

(73) Assignee: avateramedical GmbH

( * ) Notice: Subject to any disclaimer, the term of this patent is extended or adjusted under 35 U.S.C. 154(b) by 423 days.

(21) Appl. No.: 15/897,501

(22) Filed: Feb. 15, 2018

(65) Prior Publication Data

US 2018/0228343 A1 Aug. 16, 2018

(30) Foreign Application Priority Data

Feb. 16, 2017 (DE) .................. 10 2017 103 198

(51) Int. Cl.
*A61B 1/00* (2006.01)
*A61B 34/20* (2016.01)
(Continued)

(52) U.S. Cl.
CPC ...... *A61B 1/00009* (2013.01); *A61B 1/00004* (2013.01); *A61B 1/00045* (2013.01); *A61B 1/00193* (2013.01); *A61B 1/045* (2013.01); *A61B 5/06* (2013.01); *A61B 34/20* (2016.02); *A61B 34/25* (2016.02); *A61B 34/35* (2016.02); *A61B 1/00039* (2013.01); *A61B 1/042* (2013.01); *A61B 5/7415* (2013.01);
(Continued)

(58) Field of Classification Search
CPC ............ A61B 1/00009; A61B 1/00004; A61B 1/00043; A61B 1/000193; A61B 1/045; A61B 1/00039; A61B 5/06; A61B 34/20; A61B 34/35; A61B 2034/2059; A61B 2090/365; A61B 2090/364
See application file for complete search history.

(56) References Cited

U.S. PATENT DOCUMENTS

| 4,895,431 A | 1/1990 | Tsujiuchi et al. |
| 5,749,362 A | 5/1998 | Funda et al. |
| (Continued) | | |

FOREIGN PATENT DOCUMENTS

| DE | 3738667 | 5/1988 |
| DE | 69322202 T2 | 7/1999 |
| (Continued) | | |

OTHER PUBLICATIONS

German Search report for counterpart application dated Sep. 14, 2017 (14 pages).

*Primary Examiner* — John P Leubecker
(74) *Attorney, Agent, or Firm* — Harness, Dickey & Pierce, P.L.C.

(57) ABSTRACT

A device to set and retrieve a reference point during a surgical procedure. The device (12) has an endoscope (312) which captures several images successively as an image sequence and generates image data corresponding to the image sequence, which data are then processed and output on at least one display unit (44). A control unit (40) determines the first position of a first point at a first point in time, a second position of a second point at a second point in time, and a first distance vector between the first position and the second position. The positions are determined via the kinematic chain of a manipulator arm (16a,16b).

18 Claims, 6 Drawing Sheets

(51) Int. Cl.
  *A61B 5/06* (2006.01)
  *A61B 34/00* (2016.01)
  *A61B 34/35* (2016.01)
  *A61B 1/045* (2006.01)
  *A61B 1/04* (2006.01)
  *A61B 5/00* (2006.01)
  *A61B 90/00* (2016.01)
  *A61B 34/30* (2016.01)

(52) U.S. Cl.
  CPC ..... *A61B 5/7455* (2013.01); *A61B 2034/2065* (2016.02); *A61B 2034/302* (2016.02); *A61B 2090/365* (2016.02)

(56) References Cited

U.S. PATENT DOCUMENTS

| | | | | |
|---|---|---|---|---|
| 8,792,963 B2* | 7/2014 | Zhao | ...................... | B25J 9/1689 600/424 |
| 9,055,881 B2* | 6/2015 | Gilboa | ............... | A61B 1/00128 |
| 9,155,592 B2* | 10/2015 | Itkowitz | ................. | A61B 34/30 |
| 10,004,387 B2* | 6/2018 | Prisco | ................. | A61B 1/0005 |
| 2002/0077544 A1* | 6/2002 | Shahidi | ................. | A61B 90/36 600/424 |
| 2006/0276686 A1* | 12/2006 | Tsuji | ...................... | A61B 34/20 600/117 |
| 2008/0004603 A1* | 1/2008 | Larkin | ...................... | A61B 1/04 606/1 |
| 2009/0043161 A1* | 2/2009 | Doi | .................... | A61B 1/00181 600/117 |
| 2013/0283205 A1* | 10/2013 | Suzuno | ................ | G01C 21/367 715/784 |
| 2015/0161802 A1* | 6/2015 | Christiansen | .......... | A61B 90/94 348/74 |
| 2016/0073927 A1* | 3/2016 | Akimoto | ............ | A61B 1/00009 600/109 |
| 2016/0151115 A1 | 6/2016 | Karguth et al. | | |
| 2016/0228075 A1* | 8/2016 | Kitamura | ........... | A61B 1/00009 |
| 2016/0361122 A1 | 12/2016 | Seeber | | |
| 2016/0361128 A1 | 12/2016 | Seeber | | |
| 2017/0181798 A1* | 6/2017 | Panescu | ................. | A61B 34/37 |
| 2018/0098685 A1* | 4/2018 | Osawa | ................. | A61B 1/0005 |
| 2018/0098690 A1* | 4/2018 | Iwaki | ................. | A61B 1/00009 |
| 2018/0296280 A1* | 10/2018 | Kurihara | ............ | A61B 1/00006 |
| 2018/0368919 A1* | 12/2018 | Pfeifer | ..................... | G01C 3/14 |

FOREIGN PATENT DOCUMENTS

| | | |
|---|---|---|
| DE | 102012211396 A1 | 4/2014 |
| DE | 102015109368 A1 | 12/2016 |
| DE | 102015109371 A1 | 12/2016 |
| EP | 2046538 B1 | 12/2011 |
| EP | 2411966 B1 | 5/2016 |
| JP | 09149876 A * | 6/1997 |

* cited by examiner

DEVICE TO SET AND RETRIEVE A REFERENCE POINT DURING A SURGICAL PROCEDURE

CROSS-REFERENCE TO RELATED APPLICATIONS

This application claims the benefit and priority of DE 10 2017 103 198.7 filed Feb. 16, 2017. The entire disclosure of the above application is incorporated herein by reference

FIELD

The invention relates to a device to set and retrieve a reference point during a surgical procedure. The device comprises an endoscope which captures several images successively as an image sequence and generates image data corresponding to the images. At least one control unit processes the image data and outputs images corresponding to the image data on at least one display unit. By a user input via a user interface, a reference point that shall be retrievable in the further course of the surgery is set.

SUMMARY

The device is used in particular in a system for robot-assisted surgery, in particular for a telerobot-assisted procedure. The system has at least one manipulator arm connected to the endoscope and/or one manipulator arm connected to a surgical instrument for tissue manipulation. Such systems are also referred to as manipulators or telemanipulators or surgical robots.

In the documents DE 10 2015 109 368 and DE 10 2015 109 371, devices and methods for telerobot-assisted surgery are disclosed.

In minimally-invasive surgeries, in particular in the laparoscopy, the surgical instruments required for tissue manipulations during the surgery are inserted into the patient to be operated through so-called trocars. In addition to the surgical instruments to be inserted for tissue manipulation, an endoscope is inserted into the body of the patient through a further trocar for capturing images of the operative situs during the surgery. During surgery, the surgeon uses the live image of the operative situs displayed on a display unit to orient himself/herself, to be able to determine necessary tissue manipulations and to be able to perform them in real time as well as to be able to make decisions relevant for the course of therapy. For this, the surgeon has at least a part of the end effectors of the instruments with which he/she manipulates the tissue in the field of view of the endoscope. This procedure is the same both in manually performed surgeries with manually actuatable surgical instruments and in surgeries performed by a telemanipulator in a robot-assisted surgery. When using a telemanipulator, the position and the orientation of the surgical instruments as well as the position and the orientation of the endoscope are guided by way of manipulator arms of the telemanipulator. The surgeon operates the manipulator arms and the surgical instruments by remote control using haptic input devices.

In the course of a surgery, it may be necessary for the surgeon that he/she orients the endoscope to certain anatomic features or structures so that he/she in particular has a good view on tissue to be manipulated or on sudden bleeding. Only in this way it is possible for the surgeon to visually examine the relevant features or structures and to make decisions on the further course of therapy. In this connection, it may happen that a surgical instrument or several surgical instruments disappear from the field of view of the endoscope so that the surgeon no longer has a visual control over the instruments. However, for tissue manipulation a visual control is compulsory, so that prior to a tissue manipulation the surgeon has to re-orient the endoscope such that the instruments that he/she wants to use for tissue manipulation are in the field of view. Basically, for patient safety, a movement of the instruments without a visual control should be prevented.

From document EP 2411966 B1, a system for providing visual guidance for steering a tip of an endoscopic device towards one or more landmarks and assisting an operator in endoscopic navigation is known.

From document EP 2046538 B1 a system is known, in which an identification indicator and the position of a surgical instrument in a boundary area of a computer display screen are displayed.

It is an aspect of the invention to specify a device to set and retrieve a reference point during a surgical procedure, by which it is made easier for the surgeon to retrieve the reference point during a surgical procedure.

This object is solved both by a device to set and retrieve a reference point during a surgical procedure having the features of claim 1 and by a device having the features of claim 2. Advantageous embodiments are specified for both devices in the dependent claims.

Owing to the determined distance vector between the first position and the second position, the set reference point or the surgical instrument can easily be retrieved by means of the information based on the distance vector, wherein a surgeon is able to move the endoscope in particular such that the reference point or the surgical instrument again comes into the field of view of the endoscope.

Generally, the invention has the purpose to create information that can be used to enable the surgeon by way of the output of visual, haptic or acoustic signals to orient the endoscope such that the instruments and/or another reference point are again in the field of view of the endoscope. When outputting visual information in connection with a 3D display, such as a stereoscopic display, a direction information can be displayed in particular as a 3D vector. Further, the invention has the purpose that during a surgery a surgeon can define a reference point or a virtual landmark in the operative situs, wherein an information is created which enables the surgeon to retrieve this reference point by the output of visual, haptic or acoustic signals. As a result, it is in particular possible for the surgeon to orient the endoscope such that the reference point appears in the field of view of the endoscope.

It is advantageous when the control unit marks an area around a set reference point, i.e. around the set first reference point or a set further reference point, by means of a marking or when the control unit marks an area around a set reference point of the surgical instrument by means of a marking. This reference point of the surgical instrument can be the instrument tip, in particular the tip of the end effector or an interface between shaft and end effector. The reference point or the reference point on the surgical instrument thus serves as a point of orientation. Owing to the known kinematic structure or the kinematic chain the exact coordinates of the points, in particular of the points of orientation and of the reference points can be determined. The information that is output and that is based on the distance vector serves as a guidance when moving the endoscope in order to bring, for example, the reference point of the surgical instrument or a previously set reference point into the field of view of the endoscope.

A marking of the area around the set reference point preferably takes place in that an organ at the reference point or an organ in close vicinity to the reference point or a tissue structure at the reference point or in close vicinity to the reference point is detected in particular by a pattern recognition method, and this organ or this tissue structure is provided with a marking. In particular, the tissue structure or the organ can be displayed in color for marking. Thus, using the set reference points that serve as anatomic landmarks, it is easily possible to recognize the organ or the tissue structure at set reference points by means of an image subsequently captured by the endoscope in that an extraction of suitable object features for classifying the organ or the tissue structure or the reference point takes place.

It is particularly advantageous when the control unit captures an image detail of the surrounding of the determined first position during determination of the first position and, for retrieving the first position, compares it in a further image captured after determination of the first position with at least an image detail of the further image. For this, the control unit can in particular implement methods for pattern recognition of tissue structures and for pattern recognition of organs. Alternatively or additionally, an automatic retrieving of the first position by way of the control unit can take place by implementing a method for correlation between the stored object features of an object detected at the first position and the object features extracted from a respective currently captured image. The automatic retrieving by image comparison in particular takes place taking into account rotation, translation, scaling and deformation, wherein, for example, a so-called warping method is employed. As a result, a retrieving and preferably also a marking of the first position in a further image are easily possible.

Further, it is advantageous when the control unit determines the first position based on a first image captured by the endoscope or based on the position of the endoscope at the first point in time or based on the position of the surgical instrument, and when the control unit determines the second position based on a second image captured by the endoscope after the first image or based on the position of the endoscope at the second point in time. As a result, the position of the point does not have to be determined in a complex manner but can easily be determined from the position of the endoscope or the position of the surgical instrument.

Further, it is advantageous when the control unit determines the positions each time via the kinematic chain of a manipulator arm of a manipulator or of a surgical robot system that is connected to the endoscope or via the kinematic chain of a manipulator arm of the manipulator or of the surgical robot system that is connected to the surgical instrument. As a result, an easy position determination of the position of the first point, the second point and of the surgical instrument is possible. In particular, the change of the positions due to a movement of the respective manipulator arm can easily be understood and the relevant position can then easily be determined via the kinematic chain or the change of the position of the endoscope or the surgical instrument.

Further, it is advantageous when the endoscope captures a first image at the first point in time and when the endoscope captures a second image at the second point in time or when the endoscope captures a first image when determining the first position and when the endoscope captures a second image when determining the second position. As a result, when determining the positions, the image details can be compared with image details of later images. Further, the captured images can be stored and displayed once again upon request so that each of the positions can be viewed once again also at later points in time in particular during a surgery.

Further, it is advantageous when the distance of the point to the object plane is preset in the control unit as a parameter such that it, for example, has a value in the range from 0 mm to +/−20 mm. In the case of a distance of +20 mm, the point has a distance to the endoscope that is longer by 20 mm than the distance of the object plane to the endoscope. In the case of a distance of −20 mm, the point has a distance to the endoscope that is smaller by 20 mm than the distance of the object plane to the endoscope. As a result, starting from the position of the endoscope, the positions related to the optical axis of the endoscope and to the object plane can easily be set. Preferably, the value of the preset parameter may be varied by a user so that it can be set and possibly varied by the user within the range from 0.001 mm to 10 mm.

Further, it is advantageous when the distance of the point to the object plane is preset in the control unit as a parameter such that it lies within the depth of field. In an imaging optical system of an image capturing unit, the object plane is a plane running perpendicularly to the optical axis and in particular containing the object point. Only the points of the object plane are sharply imaged on the image sensor of the image capturing unit. The depth of field, often also referred to as field depth, is a measure for the extension of the sharp area in the object space of an imaging optical system. The depth of field describes the size of the distance range within which an object is imaged with sufficient sharpness. The term depth of field is, for example, defined in DIN 19040 Sheet 3.

Thus, the area in which the positions to be determined lie is restricted to an area in which the objects are still displayable with sufficient sharpness. As a result, a restriction to positions displayed with sufficient sharpness takes place, which positions are well detectable for a user so that the determination of positions in areas which are not sharply visible is prevented.

Further, it is advantageous when the endoscope, after the second image, captures and outputs at least a third image at a third point in time, as a result whereof the position, orientation, rotation, location and/or magnification of the endoscope between capturing the second image and the third image are unchanged. Here, the control unit outputs the information based on the first distance vector together with the third image. As the position of the endoscope between capturing the second and the third image has not changed, also the first distance vector has not changed so that it can easily be output together with the third image. A re-determination of the first distance vector is not necessary here.

In a further advantageous embodiment, the endoscope captures at least a further fourth image at a fourth point in time after the second image and outputs the same. The position, orientation, rotation, location and/or magnification of the endoscope are changed between the second point in time and the fourth point in time. The control unit determines the position of a point of the optical axis of the endoscope or of the axis parallel to the optical axis of the endoscope in the object plane. Alternatively, the control unit determines the position of a point of the optical axis of the endoscope or of the axis parallel to the optical axis of the endoscope at a distance to the object plane, or the position of the line segment on the optical axis of the endoscope or on the axis parallel to the optical axis of the endoscope. The position is determined at a fourth point in time as a fourth position. The control unit determines a second distance vector between the first position and the fourth position.

Further, the control unit outputs information based on the second distance vector together with an image captured at or after the fourth point in time. As a result, given a change of the position of the endoscope or of an image capturing characteristic of the endoscope the distance vector is determined newly and the newly determined distance vector is output as a basis for the information to be output with the further captured image. Thus, in the further image, a current note for retrieving the reference point can be output.

Further, it is advantageous when the control unit checks whether the determined first position is visible in a displayed image. Here, the endoscope has captured the displayed image after the first point in time. The control unit inserts an optical marking at the first position into the displayed image. As a result, an easier retrieving of the first position serving as a reference point is possible since by means of the optical marking a viewer is given an indication for retrieving the first position.

It is further advantageous when the control unit generates a vector arrow on a portion of a line between the center of the displayed image in the direction of the first position and inserts it into the displayed image. As a result, a viewer is given a clear indication in which direction the reference point is located. The vector arrow itself or an additional or alternative marking can also be inserted in a boundary region of the displayed image. The vector itself is preferably determined in a three-dimensional coordinate system, such as a three-dimensional patient coordinate system or a three-dimensional instrument coordinate system. The vector arrow is preferably inserted as a three-dimensional arrow into a three-dimensional image representation. In this way, the viewer is given an easily detectable indication in which direction the reference point, starting from the displayed image, is located so that it can easily be found again by a suitable positioning of the endoscope.

Here, it is advantageous when at least a second reference point is set by a user input via a user interface or automatically by the control unit. Dependent on a preset selection parameter, the control unit can optionally generate a first vector arrow and/or a second vector arrow and insert it into the displayed image. The first vector arrow and/or the second vector arrow are preferably displayed in different colors or have different markings, in particular different color markings. Thus, it is easily possible to assign the vector arrows to the respective reference point so that a desired reference point can easily be found again. Additionally or alternatively to the vector arrows also other markings can be inserted into the displayed image.

Here, it is further advantageous when the control unit graphically and/or acoustically outputs a selection menu with displayable and/or stored reference points. Via the selection menu, displayable reference points are selectable, i.e. reference points with respect to which information can be inserted into the image. Further, via the selection menu also additional or alternative reference functions can be activated and deactivated, for example an acoustic information or a haptic information. Alternatively or additionally, displayable and/or stored reference points are selectable via voice commands which may, for example, be input via a microphone and are processable by a control unit. Further, alternatively or additionally the displayable and/or stored reference points can be selected by body gestures which are, for example, captured by a camera and evaluated by a control unit, in particular with the aid of finger gestures, which are, for example, sensed using a touch sensitive surface, such as a touchpad or a touch sensitive screen, and are evaluated using the control unit.

In the inventive devices or one of the mentioned developments, it is further advantageous when the control unit outputs an acoustic signal dependent on the value of the determined distance vector or a visual information dependent on the value of the determined distance vector or a haptic information for signaling the direction of movement towards the reference point via a manual input device of a user interface. The visual information dependent on the value of the determined distance vector can be output in particular via the length of the displayed vector arrow or by the output of the value as a series of digits in particular with a unit of length for specifying the distance. As a haptic information for signaling the direction of movement towards the reference point, a counterforce, a so-called force feedback can be implemented. As an acoustic signal, a tone sequence with a distance-dependent frequency of the distances between the tones of the tone sequence can be provided, in particular such that given a long distance between the points, i.e. given a high vector value, the tones of the tone sequence have a long distance to each other, the distance becoming smaller in the case of a smaller value of the vector, preferably up to the output of a continuous tone.

Further, it is advantageous when the control unit inserts a first reference point and possibly a further reference point as a respective reference point marking or as a marking of an object present at the reference point in a 3D model of a patient to be operated. This 3D model can then be used for visualization and/or documentation of the course of the surgery. The object present in the vicinity of the reference point can, for example, be an organ or a certain tissue structure which is then preferably completely marked in the 3D model.

Further, it is advantageous when the endoscope is a stereo endoscope with a common optical axis. The control unit can then determine the first, second, third and/or fourth position as a position of a point of the common optical axis of the stereo endoscope in the object plane, or as a position of a point of the optical axis of the stereo endoscope at a distance to the object plane, or as a position of a line segment on the optical axis of the stereo endoscope with a point in the object plane. Alternatively, the endoscope can be a stereo endoscope with two separate imaging optical systems, the optical axes of which are parallel, wherein the control unit determines the first, second, third and/or fourth position as a position of a point of an axis running between the optical axes of the stereo endoscope in the object plane, or as a position of a point of an axis running between the optical axes of the stereo endoscope at a distance to the object plane, or as a position of a line segment on the axis running between the optical axes of the stereo endoscope with a point in the object plane. The axis running between the optical axes of the stereo endoscope preferably runs in the middle between the optical axes.

Thus, the invention can also easily be used in connection with stereo endoscopes.

A second aspect of the invention relates to a system for robot-assisted surgery, in particular for a telerobot-assisted procedure with an inventive device or a further above-indicated development, the user interface comprising at least one input device for the input of at least one input command. The control unit and/or a further control unit controls actuators of the system for robot-assisted surgery such that the endoscope connected to a manipulator arm and/or a surgical instrument for tissue manipulation connected to a further manipulator arm is positioned dependent on the input command by at least one of the drive units of the system, preferably by at least one drive unit of the manipulator arm.

As a result, a telerobot-assisted procedure during a surgery is made easier. In particular, a user, such as a surgeon, can easily set reference points which he/she can then easily retrieve by means of the inventive approach. As a result, the orientation in the body of a patient to be operated is considerably made easier.

A third aspect of the invention relates to a method to set and retrieve a reference point during a surgical procedure, in which by an endoscope several images are successively captured as an image sequence and image data corresponding to the images are generated. The image data are processed by at least one control unit and images corresponding to the image data are output. The position of a point of the optical axis of the endoscope or of an axis parallel to the optical axis of the endoscope in the object plane, or the position of a point of the optical axis of the endoscope or of the axis parallel to the optical axis of the endoscope at a distance to the object plane, or the position of a line segment on the optical axis of the endoscope or on an axis parallel to the optical axis of the endoscope with a point in the object plane is determined as a first position at a first point in time. The first position is set as a first reference point by a user input via a user interface. The position of a point of the optical axis of the endoscope or of the axis parallel to the optical axis of the endoscope in the object plane, or the position of a point of the optical axis of the endoscope or of the axis parallel to the optical axis of the endoscope at a distance to the object plane, or the position of the line segment on the optical axis of the endoscope or on the axis parallel to the optical axis of the endoscope is determined as a second position at a second point in time. Between the first position and the second position a first distance vector is determined. An information based on the first distance vector is output together with an image captured at or after the second point in time.

A fourth aspect relates to a system to set and retrieve a reference point during a surgical procedure, in which by an endoscope several images are successively captured as an image sequence and image data corresponding to the images are generated. By at least one control unit the image data are processed and images corresponding to the image data are output. The position of a surgical instrument is determined as a first position. Further, the position of a point of the optical axis of the endoscope or of an axis parallel to the optical axis of the endoscope in the object plane, or the position of a point of the optical axis of the endoscope or of the axis parallel to the optical axis of the endoscope at a distance to the object plane, or the position of a line segment on the optical axis of the endoscope or on an axis parallel to the optical axis of the endoscope with a point in the object plane is determined as a second position. Between the first position and the second position a first distance vector is determined. An information based on the first distance vector is output together with the image captured when determining the first position.

The methods according to the third and fourth aspect can be developed in the same manner as indicated above for the devices.

Further features and advantages result from the following description which explains the invention in more detail on the basis of embodiments in connection with the enclosed Figures.

DRAWINGS

DETAILED DESCRIPTION

Figure 1:
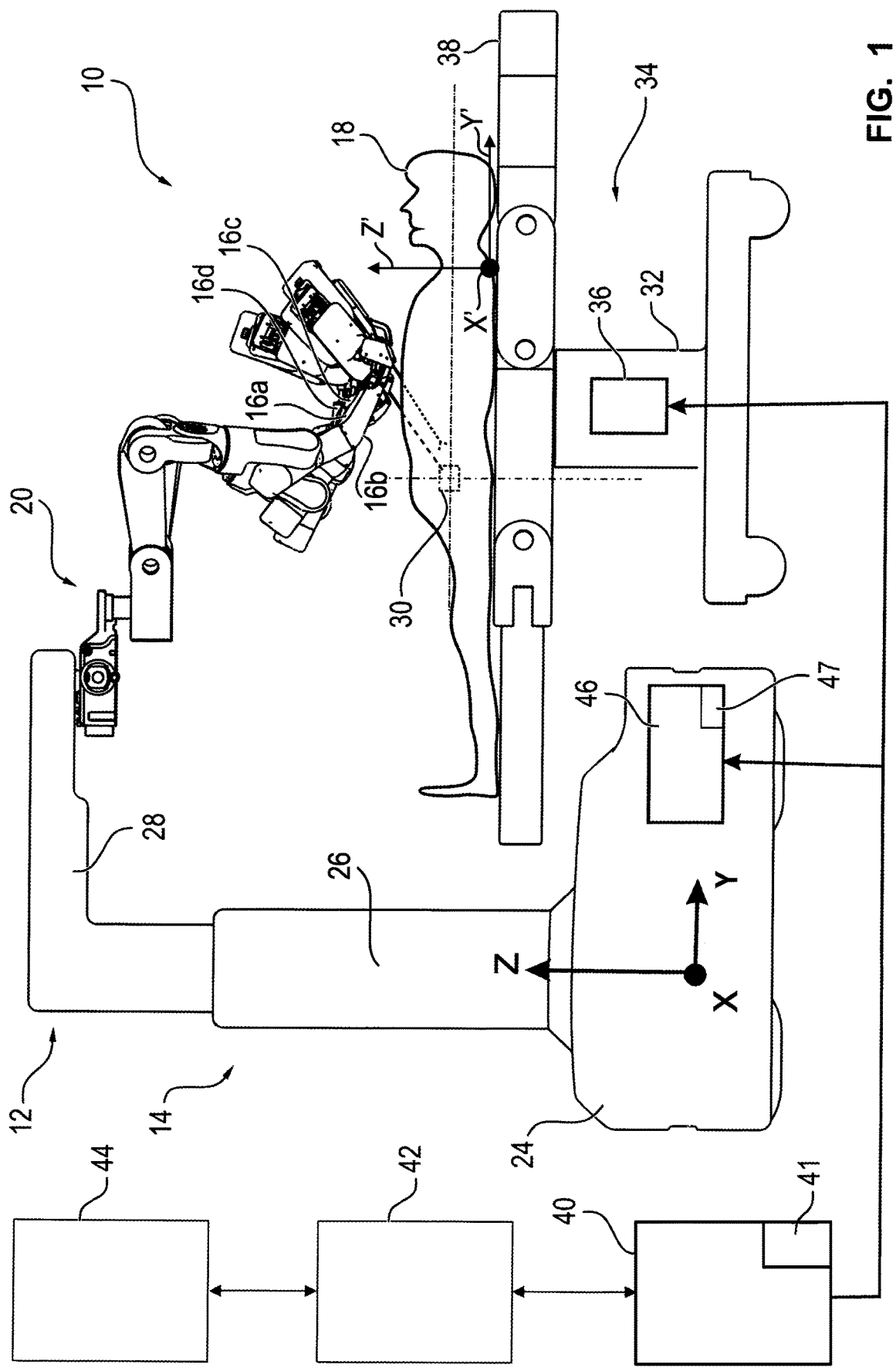
FIG. 1 shows a schematic side view of a patient and a system for robot-assisted surgery comprising a manipulator having four manipulator arms, to which one instrument unit each is connectable.

FIG. 1 shows a schematic side view of a patient 18 and a system 10 for robot-assisted surgery with a manipulator 12 having a stand 14 and four manipulator arms 16a to 16d. The manipulator 12 is generally also referred to as apparatus for robot-assisted surgery. The system 10 serves to perform a surgery on a patient 18 positioned on an operating table 34. Based on the anatomy of the patient 18 and the surgery to be performed, there result the coordinates $x'_z$, $y'_z$, $z'_z$ of a surgical area 30 in a patient coordinate system $X'$, $Y'$, $Z'$. The manipulator 12 has a coordinate system $X$, $Y$, $Z$ of the apparatus 12, the coordinate origin of which is arranged in a stand base 24 of a stand 14 of the manipulator 12. The stand 14 has a traverse 26 firmly connected to the stand base 24 and with which an L-shaped stand arm 28 is connected, at the end of which that is remote from the stand base 24 the manipulator arms 16a to 16d are connected via a stand head 20.

The operating table 34 has an operating table column 32 in which a control unit 36 of the operating table 34 is arranged and on which a patient support surface 38 comprising several segments is arranged. The control unit 36 serves to control the movement of elements of the operating table 34, in particular for length adjustment of the operating table column 32 and thus for adjusting the height of the patient support surface 38 and for adjusting individual segments as well as the tilt and the swing of the patient support surface 38. Preferably, however, the adjustment of the segments of the operating table 34 is blocked during a surgery by means of the manipulator 12. The system 10 further comprises a control unit 46 of the manipulator 12 as well as a central control unit 40, the central control unit 40 being connected to the control unit 46 of the manipulator 12, the control unit 36 of the operating table 34 as well as a control panel 42 with a display unit 44 via data lines. The control unit 40 has an output unit 41 and the control unit 46 has an output unit 47, by each of which optical and/or acoustic signals can be output.

The surface of the patient support surface 38 forms a frontal plane on which the patient 18 is positioned. Further, through the coordinate origin of the patient coordinate system $X'$, $Y'$, $Z'$ a transversal plane in which the coordinate axes $X'$ and $Z'$ lie runs. Further, a median plane in which the coordinate axes $Z'$ and $Y'$ lie runs through the coordinate origin.

The coordinates $x'_z$, $y'_z$, $z'_z$ of the surgical area 30 in the patient coordinate system $X'$, $Y'$, $Z'$ are known and, due to the known position of the patient coordinate system $X'$, $Y'$, $Z'$ with respect to the coordinate system $X$, $Y$, $Z$ of the apparatus 12, they can easily be taken into account in the control of the manipulator arms 16a to 16d as well as the instrument unit connected to the manipulator arms 16a to 16d for performing a surgery using the manipulator 12, in particular can be converted into coordinates $x_z$, $y_z$, $z_z$ of the coordinate system X, Y, Z of the apparatus.

Figure 2:
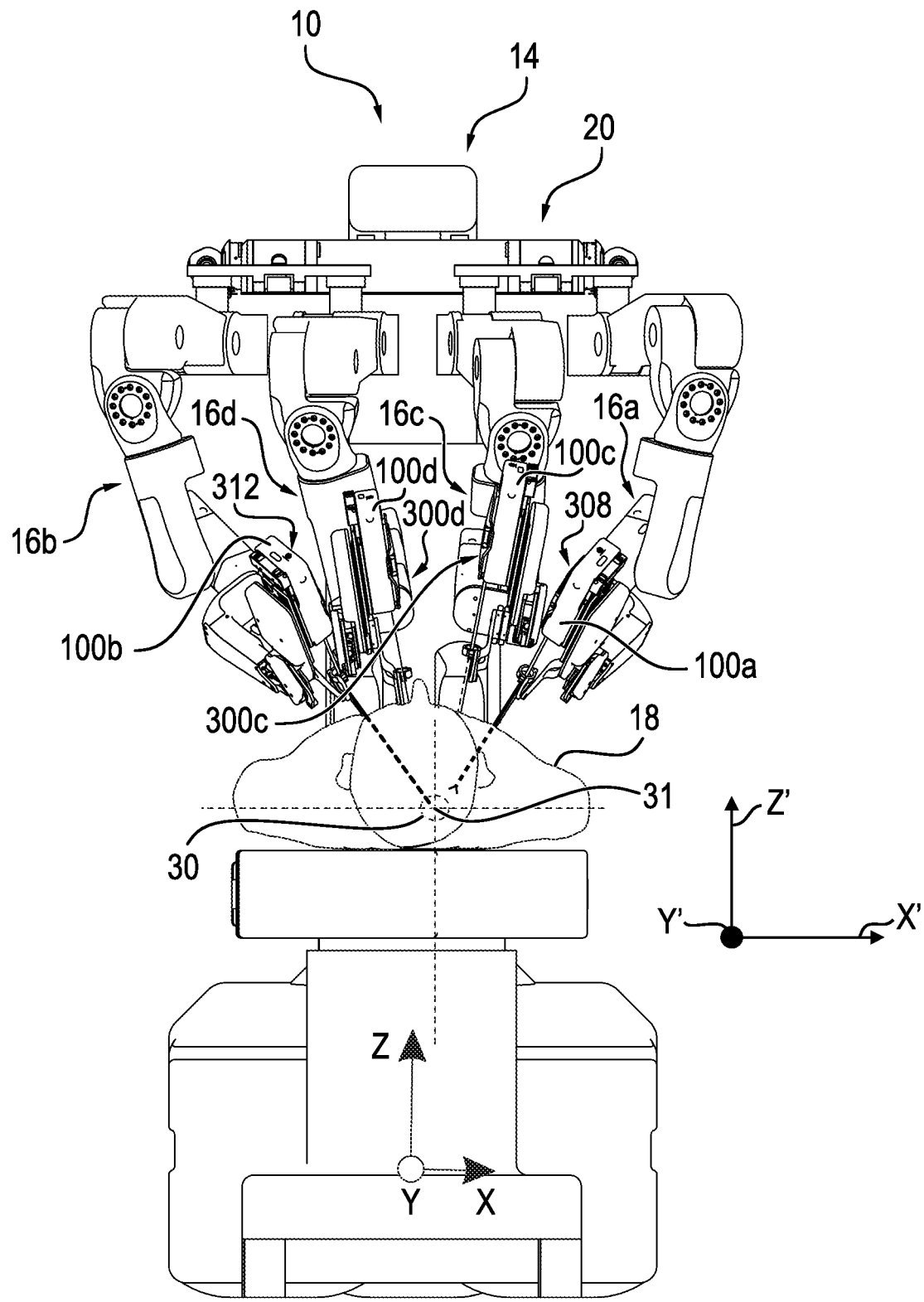
FIG. 2 shows a schematic front view of the patient and the system according to FIG. 1.

FIG. 2 shows a schematic front view of the patient 18 and of the system 10 according to FIG. 1. At the proximal end of the manipulator arms 16a to 16d one coupling unit 100a to 100d each is arranged, to each of which one instrument unit 308 to 300d for performing the surgery is connected. The instrument units 300c, 300d, 308, 312 are connected to coupling units 100a, 100b, 100c, 100d of the manipulator arms 16a to 16d. The instrument shafts of the instrument units 300c, 300d, 308, 312 are inserted via trocars into the body of the patient 18 at least with their end remote from the manipulator arm 16a to 16d and can be moved and positioned by the manipulator arms 16a to 16d such that they are arranged in the surgical area 30. As a result, the end effector present at the ends of the instrument shafts remote from the manipulator arms 16a, 16c and 16d can be used for tissue manipulations and other manipulations required for therapy in the surgical area 30. Also the tip of an endoscope 312 connected to the manipulator arm 16b can be moved up into the surgical area 30 for capturing images of the surgical area 30. By the manipulator arm 16b, the endoscope 312 can be moved and positioned such that images of different regions of the surgical area 30 can be captured to allow the surgeon a good view on the regions of the surgical area 30 relevant for treatment.

By means of the broken lines running through the surgical area 30 and running parallel to the coordinate axes X' and Z', the coordinates $y'_z$, $z'_z$ of the center 31 of the surgical area 30 with respect to the coordinate axes X' and Z' are indicated. Even if the patient coordinate system X', Y', Z' in FIGS. 1 and 2 has been drawn relative to the coordinate system X, Y, Z of the manipulator only with a linear displacement for reasons of clarity, both coordinate systems may also be arbitrarily oriented to each other dependent on the surgery. Further, their relationship does not have to be fixed so that the position of the patient coordinate system X', Y', Z' may vary during surgery.

Figure 3:
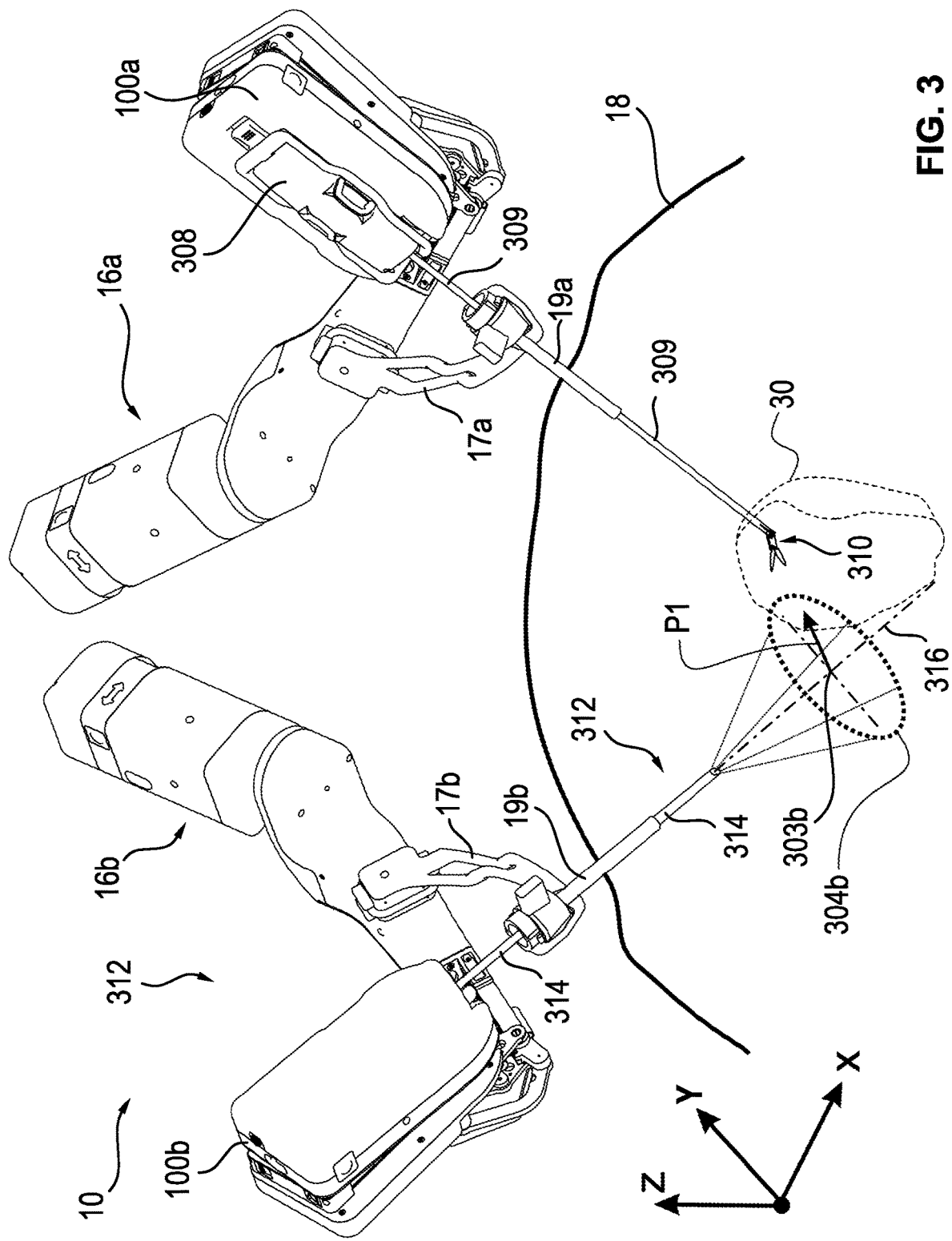
FIG. 3 shows a detail of the patient and of the system according to FIGS. 1 and 2.

FIG. 3 shows a part of the patient 18 and a detail of the system 10 according to FIGS. 1 and 2. Specifically, the instrument-side arm ends of the manipulator arms 16a and 16b as well as a schematic sectional view of the patient body 18 with the relevant surgical area are illustrated. An instrument unit 312 in the form of an endoscope 312 is connected to the coupling unit 100b of the manipulator arm 16b. The endoscope 312 is designed as a rod endoscope and serves to capture images inside the body of the patient 18. The end of the rod 314 of the endoscope 312 remote from the coupling unit 100b is inserted into the body of the patient 18 through a trocar 19b held by a trocar holder 17b and may be varied in its position relative to the patient 18 by the manipulator arm 16b as a result of operating inputs of a user, in particular the surgeon, via an input unit of the operating device 42. As a result, the rod 314 can in particular be moved further into the patient body as well as in opposite direction. Also the angle of the rod 314 of the endoscope 312 can be varied by a corresponding movement of the manipulator arm 16b, in particular in the direction of the arrow P1 shown in FIG. 3 in order to capture images of further regions of the surgical area 30 and in particular images of end effectors 310 present in the surgical area 30.

The end effector 310 of the instrument unit 308 is arranged at the end of the instrument shaft 309 of the instrument unit 308 remote from the coupling unit 100a, wherein, dependent on the operating inputs at the control panel 42, the instrument unit 308 can be moved and controlled such that both the position of the end effector 310 in the surgical area 30 can be changed and different movements of the end effector 310 can be performed and functions of the end effector 310 can be activated. In the present case, the end effectors are gripping pliers that can be bent at the shaft end of the instrument shaft 309 by up to 90 degrees. Instead of the instrument unit 308, however, also alternative instrument units can be connected to the coupling unit 100a. The end effector 310 may, however, also be a monopolar surgical instrument for high-frequency surgery which is powered with electrical energy via the coupling unit 100a and the instrument shaft 309.

The end effector 310 insertable into the body opening of the patient 18 through the trocar 19a may also comprise a clamp, a pair of scissors, a gripper, a needle holder, a micro dissector, a clamping device, a rinsing and/or suction device, a cutting blade, a cautery probe, a catheter and/or a suction nozzle. As a result thereof, the surgical instrument provided by the instrument unit 308 may optionally have different end effectors which can be used for common minimally invasive surgeries, in particular in the laparoscopic surgery. However, also other surgical instruments may be used additionally or alternatively. In particular, a further endoscope and/or an additional illumination unit may be provided by the use of a corresponding instrument unit 308 so that these may then be used during surgery in the surgical area 30.

The endoscope 312 is connected to the coupling unit 100d of the manipulator arm 16b via optical and/or electrical transmitting means. These may be designed as interfaces or may be integrated in interfaces. The transmitting means serve for camera control and/or image data transmission and/or image signal transmission. Optical fiber connections may also be provided, in particular to guide illumination light up into the surgical area 30. The shaft 309 of the surgical instrument of the instrument unit 308 is inserted into the patient via a body opening of the patient 18 through a trocar 19a held by a trocar holder 17a on the manipulator arm 16a and moved up into the surgical area 30. Inside the shaft 314, the endoscope 312 has an optical imaging system, the optical axis 316 of which is illustrated by the dash-dotted line in FIG. 3. This optical imaging system may comprise a fixed optical system or a zoom optical system. The imaging optical system defines an object plane which is schematically illustrated in FIG. 3 by a circle representation, placed in the three-dimensional space, for the image capturing area of the endoscope 312 and is identified with the reference sign 304b. The object plane 304b is generally also referred to as focusing plane. The point of intersection between the optical axis and the object plane 304b is identified in FIG. 3 with the reference sign 303b. When the endoscope 312 is pivoted by the manipulator arm 16b such that the optical axis 316 is shifted or pivoted in the direction of the arrow P1, then a different region of the surgical area 30 is detected by the endoscope 312 so that the endoscope captures images of this region of the surgical area 30, which can then be output on the display unit 44. When the endoscope 312 is pivoted so far that the optical axis 316 touches the arrow tip of the arrow P1, the image capturing area of the endoscope 312 has been displaced so far that also the end effector 310 of the surgical instrument of the instrument unit 308 is located in the image capturing area of the endoscope 312 and an image of the end effector 310 is visible in an image captured by the endoscope 312 and displayed on the display unit 44.

Figure 4:
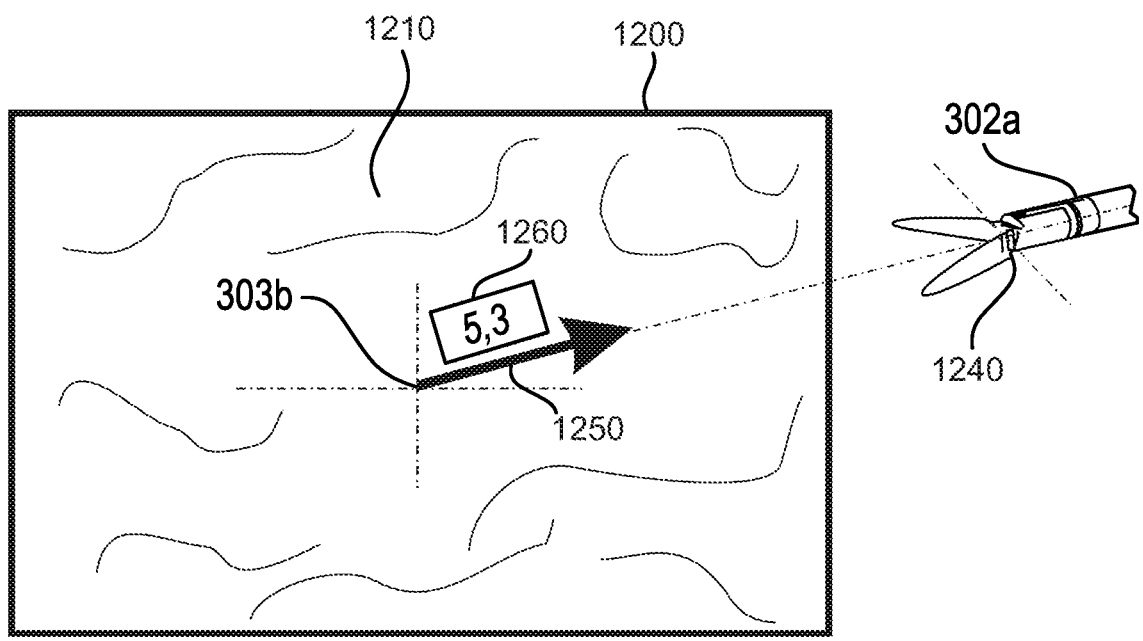
FIG. 4 shows a field of view displayed as an image on a display unit together with an instrument present outside the field of view.

FIG. 4 shows an image 1200 of the field of view captured by the endoscope 312, which image is displayed on the display unit 44. In the displayed image 1200, the visible tissue structures 1210 in the surgical area 30 as well as further pieces of information are displayed. The crossing dash-dotted lines in the center of the displayed image 1200 show the point of intersection 303b of the optical axis 316 of the endoscope 312 and the object plane 304b. The end effector 310 is located outside the field of view of the endoscope 312 and is thus not illustrated in the image 1200 displayed by the display unit 44. A point of rotation 1240 at the front end of the bendable instrument shaft 309 is used as a reference point of the end effector 310 in the previous embodiment. In other embodiments also other points of the end effector can be used as reference points. Between the point of intersection 303b and the reference point 1240 the distance vector in the three-dimensional space, preferably in the three-dimensional device coordinate system X, Y, Z of the manipulator 12 is determined by the control unit 40. The value of the vector is optionally inserted into the displayed image 1200 as distance information 1260. The illustrated arrow 1250 extends in a section of the vector. The vector is defined by the line segment between the point of intersection 303b and the reference point 1240. Alternatively or additionally, the length of the displayed arrow 1250 can be dependent on the value of the vector. I.e. when the end effector 310 has a longer distance to the field of view of the endoscope 312 and thus a longer distance to the point of intersection 303b, a longer arrow 1250 is displayed and when the distance is shorter a shorter arrow 1250 is displayed in the displayed image 1200.

Thus, by the displayed arrow 1250 the end effector 310 can easily be found in the surgical area 30 when the end effector 310 itself is not visible in the image 1200 output by the display unit 44 since it is located in a non-displayed region of the image captured by the endoscope 312 or outside the field of view of the endoscope 312.

Figure 5:
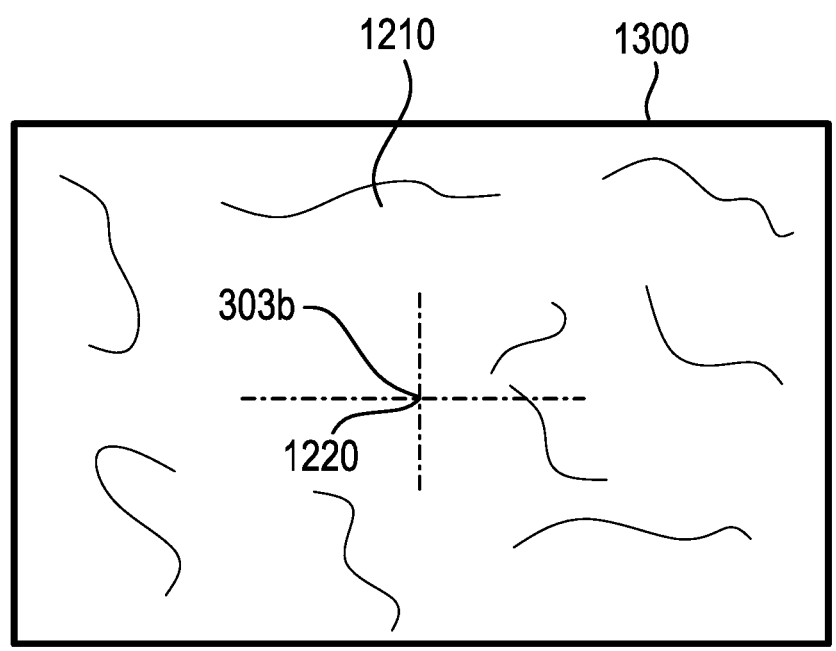
FIG. 5 shows a field of view displayed as an image on a display unit during the marking of a reference point.
Figure 6:
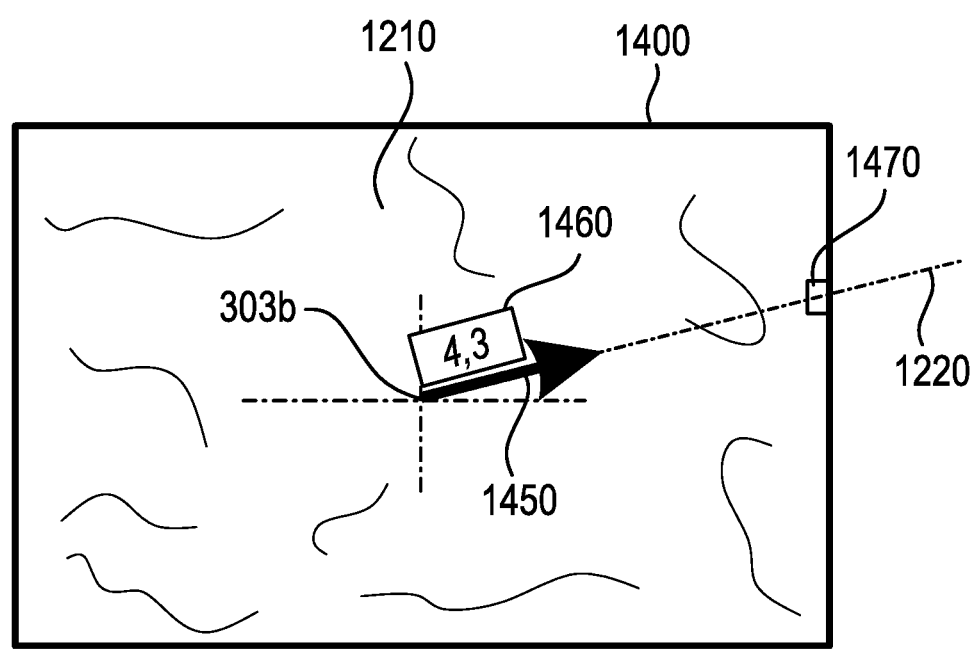
FIG. 6 shows a field of view displayed as an image on a display unit together with a reference point located outside the field of view.

FIG. 5 shows a field of view of the endoscope 312, which field of view is displayed on the display unit 44 as an image 1300. The position of the point of intersection 303b between the optical axis of the endoscope 312 and the object plane 304b can unambiguously be determined in the device coordinate system X, Y, Z via the kinematic chain of the joints and segments of the manipulator arm 16b. By corresponding operating inputs via the control panel 42, the surgeon can move the manipulator arm 16b such that the endoscope 312 is positioned such that the point of intersection 303b lies at a location of the surgical area 30 that is to be marked as a reference point 1220. In the case of a corresponding operating input, a user, in particular the surgeon, can mark this point as a reference point, wherein its position is stored so that the position is available at a later point in time given an activation of a function for retrieving a previously marked reference point 1220. In addition, the position of this reference point 1220 can be marked in the image 1300, and also in further displayed images a marking can be inserted at the position of the stored reference point 1220 so that it is well visible for the surgeon in the image 1300. If, subsequently, the endoscope 312 is pivoted such that the reference point 1220 is arranged outside the displayed image 1400, as shown in FIG. 6, in the image 1400 illustrated in FIG. 6 an arrow 1450 is inserted which starting from the center of the image indicates the direction in which the reference point 1220 starting from the center is located so that the surgeon is given a hint as to how he/she has to pivot the endoscope 312 so that the reference point 1220 is again in the field of view of the endoscope 312 or is again displayed in the displayed image 1400 or in a further subsequently displayed image. By such reference points 1220, of which a plurality of reference points 1220 can be set by the surgeon, locations in the situs of the patient 18 that are important for the surgery can easily be found again so that the orientation of the surgeon in the surgical area 30 is made easier, which in particular results in an improved course of surgery, which in turn may increase the safety of the patient 18 and reduce the time of surgery.

If the endoscope 312 is a stereo endoscope, the images 1200, 1300 and 1400 may also be captured and output as three-dimensional images. The arrows 1250 and 1450 can then be inserted with a corresponding orientation along the course of the determined vector into the three-dimensional image 1200, 1300, 1400 such that also the illustration of the arrows 1250 and 1450 is made in a three-dimensional manner and thus the surgeon obtains a real three-dimensional direction information. Also for the reference points 1220 according to FIGS. 5 and 6, a numerical value information 1460 for specifying the distance between the point of intersection 303b and the reference point 1220 can be displayed in addition to the direction arrow 1450. It is particularly advantageous when it can be defined via a presetting whether a numerical value 1260, 1460 is to be displayed in addition to the direction arrow 1250, 1450 or not. As an alternative to the illustrations in FIGS. 4 and 6, the direction arrow 1250, 1450 can also be displayed in a boundary area of the displayed image 1200 and 1400 so that the surgeon has a free viewing area in the center of the image 1200, 1300. Thus, both in the embodiment according to FIG. 4 and in the embodiment according to FIGS. 5 and 6 each time a distance vector of a point 303b specified by the endoscope 312 and a further point in the surgical area 30, such as the reference point 1240 of the end effector 310 or a previously set reference point 1220 is determined. Due to the known kinematic structure of the manipulator arms 16a to 16d and the instrument units 308, 300c, 300d connected to the manipulator arms as well as the endoscope 312 connected to the manipulator arm 16b, the position of the point 303b as well as of the point 1240 as well as reference points of other instrument units 300c, 300d can easily be determined at any time. A visual illustration of an arrow 1250, 1450 visualizing the distance vector as a two-dimensional illustration in a two-dimensional displayed image 1200, 1300, 1400 or as a three-dimensional arrow in a three-dimensional image 1200, 1300, 1400 serves as a guidance when moving the endoscope 312 to bring the instrument reference point 1240 or the reference point 1220 into the field of view of the endoscope 312 and thus to be able to display it in the displayed image 1200, 1300, 1400. Additionally or alternatively to the arrow 1250, 1450 inserted into the image, an acoustic signaling via the output units 47, 41 may take place in order to signalize, when moving the endoscope 312, whether the field of view of the endoscope 312 approaches the reference point 1220, 1240 or recedes therefrom. Further, additionally or alternatively, a haptic assistance for signaling the correct direction of movement given a manual input via a so-called force feedback function is possible in order to guide the manual input upon a movement of the endoscope 312 such that the reference point 1220, 1240 comes into the field of view of the endoscope 312. Setting reference points 1220 in the surgical area 30 in particular serves to set so-called anatomic landmarks. These can in particular be tissue structures relevant for the surgery or generally for orientation or organs in the surgical area 30, which are marked as a reference point 1220 by the method described. Here, it is in particular possible to recognize interconnected tissue structures, in particular organs by corresponding pattern recognition methods and to mark these tissue structures or organs altogether in the displayed image 1200, 1300, 1400 using a suitable marking.

For this, the tissue structures or the organs in the displayed image 1200, 1300, 1400 may, for example, be colored or encircled.

By the approach described in connection with FIGS. 1 to 6, the position of reference points 1220, 1240 and the position as well as the orientation of surgical instruments and end effectors 310 with respect to the field of view of the endoscope 312 or with respect to the displayed image 1200, 1300, 1400 of a visualizing device, such as the display unit 44, can easily be determined since via the kinematic chain of the manipulator arms 16a to 16d both the exact position and orientation of the endoscope 312 and the exact position and orientation of the end effectors 310 of the instruments units 308 are known. Each time, the positions and the orientations are determined with respect to the device coordinate system XYZ of the manipulator 12. The manipulator arms 16a to 16d comprise a plurality of joints which are connected to each other by rigid segments. The rotation axes of the joints are positioned in space so differently that by way of at least three joints in a working area useful for the surgery any required position and orientation both of the endoscope 312 and of the end effectors 310 is possible.

As already described in connection with FIG. 1, the manipulator arms 16a to 16d are connected to the stand 14 via the stand head 20 so that during surgery the stand head 20 offers a stationary basis just as the stand 14 itself. Starting from this common basis, for each joint the current configuration state of the joint can be determined by corresponding joint sensors and be stored and processed in the central control unit 40. Each of the joint sensors can in particular comprise a rotation angle encoder. As an alternative to the joint sensors, also stepper motors may be employed, the position of which can exactly be determined via the step control of the stepper motor. Thus, via the joint sensors or the known control of the drive units for pivoting the segments about the joints the kinematic chain of the manipulator arms 16a to 16d can precisely be determined. In particular, the length of the segments, the orientation of the joints with respect to the adjacent segments as well as the angular position and orientation of the joints with respect to the field of view of the endoscope 312 are known.

Via the kinematic chain of the manipulator arm 16b, also the position and orientation of the field of view or of the object plane 304b of the endoscope 312 can be determined in the same manner as the position and orientation of the end effectors 310 of the manipulator arms 16a, 16c and 16d. Thus, both the position of the point of intersection 303b and the position of the reference points 1240 of the end effectors 310 or other instruments or auxiliary means can easily and reliably be calculated at any time and can be used for a corresponding information output, such as via the arrows 1250, 1450. Thus, the distance vectors are possible in the three-dimensional space between the point of intersection 303b and any reference point 1220, 1240 in the three-dimensional space, in particular in the surgical area 30.

In the case of a visual information output, the representation of the information may, for example, be made by attaching a vector arrow to the point of intersection 303b displayed in the image 1200, 1400, and in particular by a spatial representation of a vector arrow in the direction of the reference point 1200, 1240. When using a three-dimensional display, this vector arrow 1250 can point in the direction of the reference point 1240, 1220 that has previously been selected.

In alternative embodiments also several reference points may be set so that then several vector arrows 1250, 1450 may be inserted into the displayed image 1200, 1300, 1400. The displayed arrows 1250, 1450 then preferably have different colors, one color each being assigned to a previously set reference point. As a result, the orientation is facilitated further so that the surgeon is provided with information about which arrow offers an information on which reference point.

The length of the displayed vector arrow 1250 can additionally or alternatively to the indication of the numerical value be used to indicate the value of the distance of the point of intersection 303b to the reference point 1220, 1240, as this was done by the arrows 1250, 1450 with different lengths in FIGS. 4 and 6. In the case of an acoustic information output, the value of the distance vector between the point of intersection 303b and the reference point 1220, 1240 can be signaled by the distance between individual tones or by the frequency of a continuous tone or by the combination of the distance between the tones of a tone sequence and the frequency of the tones of a tone sequence. When using stereo or 3D loudspeakers or stereo or 3D headphones a further spatial information can be output by a shifting of the level between the channels. This can in particular be done in a manner similar to that of known park distance control systems in passenger vehicles.

In the case of a haptic information output, the feedback to the surgeon can be effected by the generation of forces on input elements of a haptic input device such that given a movement of the endoscope 312 in a direction in which the field of view approaches the reference point 1220, 1240 such that the reference point 1220, 1240, at least in the case of a further displacement of the field of view, comes into the field of view, no or only a little counterforce acts on the input elements, and when the field of view recedes from the reference point 1220, 1240 higher forces act on the input elements so that the guidance of the hand of the surgeon takes place by the input device of the control panel 42 such that the surgeon moves the endoscope 312 intuitively by the manipulator arm 16b such that the distance vector between the point of intersection 303b and the reference point 1220, 1240 becomes smaller.

LIST OF REFERENCE SIGNS 10 system
12 manipulator
14 stand
16a to 16d manipulator arm
17a, 17b trocar holder
18 patient
19a, 19b trocar
20 stand head
24 stand base
26 traverse
28 stand arm
30 target surgical area
31 center of the target surgical area
32 operating table column
34 operating table
36 control unit of the operating table
38 patient support surface
40 central control unit of the apparatus
41 output unit
42 control panel
44 display unit
46 control unit of the manipulator
47 output unit
100, 100a to 100d coupling unit
300, 300c, 300d, 308, 312 instrument unit 309 instrument shaft
314 endoscope shaft
308 end effector
316 optical axis
303b point of intersection
304b object plane
312 endoscope
1200, 1300, 1400 displayed image
1220, 1240 reference point
1250, 1450 vector arrow
1260, 1460 numerical value
P1 direction arrow
X, Y, Z coordinate system of the device
X', Y', Z' patient coordinate system

The invention claimed is:

1. A device to set and retrieve a reference point during a surgical procedure, comprising:
an endoscope (312) which captures several images successively as an image sequence and generates image data corresponding to the images, wherein at least one control unit (40) processes the image data and outputs images (1200, 1300, 1400) corresponding to the image data on at least one display unit (44),
wherein the control unit (40) determines the position of a point of the optical axis of the endoscope (312) or of an axis parallel to the optical axis (316) of the endoscope (312) in an object plane (304b), or the position of a point of the optical axis of the endoscope (312) or of the axis parallel to the optical axis (316) of the endoscope (312) at a distance to the object plane (304b), or the position of a line segment on the optical axis (316) of the endoscope (312) or on an axis parallel to the optical axis (316) of the endoscope (312) with a point (303b) in the object plane (304b) at a first point in time as a first position, the first position being settable by a user input via a user interface as a first reference point (1220),
wherein the control unit (40) determines the position of a point of the optical axis (316) of the endoscope (312) or of the axis parallel to the optical axis (316) of the endoscope (312) in the object plane (304b), or the position of a point of the optical axis (316) of the endoscope (312) or of the axis parallel to the optical axis (316) of the endoscope (312) at the distance to the object plane (304b), or the position of the line segment on the optical axis (316) of the endoscope (312) or on the axis parallel to the optical axis (316) of the endoscope (312) at a second point in time as a second position (303b),
wherein the control unit (40) determines a first distance vector between the first position (1220) and the second position (303b),
wherein the control unit (40) outputs on the display unit (44) an information (1450, 1560) based on the first distance vector together with an image (1400) captured at or after the second point in time; and
wherein the control unit (40) determines the positions each time via the kinematic chain of a manipulator arm (16b) of a surgical robot system (10) connected to the endoscope (312) or via the kinematic chain of a manipulator arm (16a) of the surgical robot system (10) connected to a surgical instrument (308, 310).

2. The device according to claim 1, wherein the control unit (40) marks an area around a set reference point by means of a marking, or that the control unit (40) marks an area around a set reference point of the surgical instrument by means of the marking.

3. The device according to claim 1, wherein the control unit (40) captures an image detail of the surrounding of the determined first position when capturing the first position (1220) and, for retrieving the first position (1220), compares it in a further image (1400) captured after determining the first position (1220) with at least an image detail of the further image.

4. The device according to claim 1, wherein the control unit (40) determines the first position (1220, 1240) based on a first image (1200, 1300, 1400) captured by the endoscope (312) or based on the position of the endoscope (312) at the first point in time or based on the position (1240) of the surgical instrument (308), and
that the control unit (40) determines the second position (303b) based on a second image (1200, 1300, 1400) captured by the endoscope (312) after the first image (1200, 1300, 1400) or based on the position of the endoscope (312) at the second point in time.

5. The device according to claim 1, wherein the endoscope (312) captures a first image (1200, 1300, 1400) at a first point in time, and that the endoscope (312) captures a second image (1200, 1300, 1400) at the second point in time, or
that the endoscope (312) captures a first image (1200, 1300, 1400) before or upon determination of the first position and that the endoscope (312) captures a second image (1200, 1300, 1400) before or upon determination of the second position.

6. The device according to claim 1, wherein the distance of the point (303b) to the object plane (304b) is preset as a parameter in the control unit (40) such that it lies within a range from 0.001 mm to 10 mm.

7. The device according to claim 1, wherein the distance of the point (303b) to the object plane (304b) is preset as a parameter in the control unit (40) such that it lies within a depth of field.

8. The device according to claim 1, wherein after the second image (1200, 1300, 1400) the endoscope (312) captures and outputs at a third point in time at least a further third image (1200, 1300, 1400), wherein the position, orientation, rotation, location and/or magnification of the endoscope (312) between capturing the second image (1200, 1300, 1400) and the third image (1200, 1300, 1400) are unchanged,
wherein the control unit (40) outputs the information based on the first distance vector together with the third image (1200, 1300, 1400).

9. The device according to claim 1, wherein after the second image (1200, 1300, 1400) the endoscope (312) captures and outputs at least a further fourth image (1200, 1300, 1400) at a fourth point in time, and
wherein the position, orientation, rotation, location and/or magnification of the endoscope (312) between the second point in time and the fourth point in time are changed,
wherein the control unit (40) determines the position of a point (303b) of the optical axis (316) of the endoscope (312) or of the axis parallel to the optical axis (316) of the endoscope (312) in the object plane (304b), or the position of a point of the optical axis (316) of the endoscope (312) or of the axis parallel to the optical axis (316) of the endoscope (312) at the distance to the object plane (304b), or the position of the line segment on the optical axis (316) of the endoscope (312) or on the axis parallel to the optical axis (316) of the endoscope (312) at a fourth point in time as a fourth position (303b), wherein the control unit (40) determines a second distance vector between the first position (1220, 1240) and the fourth position (303b), wherein the control unit (40) outputs an information (1250, 1260, 1450, 1460) based on the second distance vector together with an image (1200, 1300, 1400) captured at or after the fourth point in time.

10. The device according to claim 1, wherein the control unit (40) checks whether the determined first position (1220) is visible in a displayed image (1200, 1300, 1400), wherein the endoscope (312) has captured the displayed image (1200, 1300, 1400) after the first point in time, and wherein the control unit (40) inserts an optical marking at the first position (1220) into the displayed image (1200, 1300, 1400).

11. The device according to claim 1, wherein the control unit (40) inserts a vector arrow (1250, 1450) extending from the center of the displayed image (1200, 1300, 1400) in the direction of the first position and inserts it into the displayed image (1200, 1300, 1400).

12. The device according to claim 11, wherein via a user interface (42) or automatically by the control unit (40) at least a second reference point is set, so that the control unit (40), dependent on a preset selection parameter, optionally generates a first vector arrow (1250) and/or a second vector arrow (1450) and inserts it into the displayed image (1200, 1300, 1400).

13. The device according to claim 12, wherein the control unit (40) outputs a selection menu with reference points (1220) available for display.

14. The device according to claim 1, wherein the control unit (40) outputs an acoustic signal dependent on the value of the determined distance vector or a visual information dependent on the value of the determined distance vector or a haptic information for signaling the correct movement direction via a manual input device of a user interface (42).

15. The device according to claim 1, wherein the control unit (40) inserts the first reference point (1220) and optionally a further reference point as a respective reference point marking or as a marking of an object present at the reference point (1220) into a 3D model of a patient (18) to be operated.

16. The device according to claim 1, wherein the endoscope (312) is a stereo endoscope with a common optical axis (316), the control unit (40) determining the first, second, a third and/or a fourth position as a position of a point of the common optical axis (316) of the stereo endoscope in the object plane (304b) or as a position of a point of the optical axis (316) of the stereo endoscope at a distance to the object plane (304b) or as a position of a line segment on the optical axis (316) of the stereo endoscope with a point (303b) in the object plane (304b), or that the endoscope (312) is a stereo endoscope with two separate imaging optical systems, the optical axes of which are parallel, wherein the control unit (40) determines the first, second, third and/or fourth position as a position of a point of an axis running between the optical axes of the stereo endoscope in the object plane (304b), or as a position of a point of an axis running between the optical axes of the stereo endoscope at a distance to the object plane (304b), or as a position of a line segment on the axis running between the optical axes of the stereo endoscope with a point (303b) in the object plane (304).

17. A system for robot-assisted surgery, in particular for a telerobot-assisted procedure, with a device (12) according to claim 1, wherein the user interface (42) comprises at least an input device for the input of at least one input command, wherein the control unit (40) or a further control unit (40) controls actuators of the system (10) for robot-assisted surgery such that the endoscope (312) connected to the manipulator arm (16b) and/or the surgical instrument (308, 310) for tissue manipulation connected to the manipulator arm (16a) is positioned by at least one drive unit dependent on the input command.

18. A device to set and retrieve a reference point during a surgical procedure, comprising:

an endoscope (312) which captures several images successively as an image sequence and generates image data corresponding to the images, wherein at least one control unit (40) processes the image data and outputs images (1200, 1300, 1400) corresponding to the image data on at least one display unit (44), wherein the control unit (40) determines the position of a point of the optical axis of the endoscope (312) or of an axis parallel to the optical axis (316) of the endoscope (312) in an object plane (304b), or the position of a point of the optical axis of the endoscope (312) or of the axis parallel to the optical axis (316) of the endoscope (312) at a distance to the object plane (304b), or the position of a line segment on the optical axis (316) of the endoscope (312) or on an axis parallel to the optical axis (316) of the endoscope (312) with a point (303b) in the object plane (304b) at a first point in time as a first position, the first position being settable by a user input via a user interface as a first reference point (1220), wherein the control unit (40) determines the position of a point of the optical axis (316) of the endoscope (312) or of the axis parallel to the optical axis (316) of the endoscope (312) in the object plane (304b), or the position of a point of the optical axis (316) of the endoscope (312) or of the axis parallel to the optical axis (316) of the endoscope (312) at the distance to the object plane (304b), or the position of the line segment on the optical axis (316) of the endoscope (312) or on the axis parallel to the optical axis (316) of the endoscope (312) at a second point in time as a second position (303b), wherein the control unit (40) determines a first distance vector between the first position (1220) and the second position (303b), wherein the control unit (40) outputs on the display unit (44) an information (1450, 1560) based on the first distance vector together with an image (1400) captured at or after the second point in time; and wherein the control unit (40) captures an image detail of the surrounding of the determined first position when capturing the first position (1220) and, for retrieving the first position (1220), compares it in a further image (1400) captured after determining the first position (1220) with at least an image detail of the further image.

* * * * *